United States Patent [19]

Krass et al.

[11] Patent Number: 4,504,671

[45] Date of Patent: Mar. 12, 1985

[54] METHOD FOR PREPARING ALDOXIME OR KETOXIME-O-ALKANOIC ACID

[75] Inventors: Dennis K. Krass, Canal Fulton; John C. Crano, Akron; Melvin S. Newman, Columbus, all of Ohio

[73] Assignee: PPG Industries, Inc., Pittsburgh, Pa.

[21] Appl. No.: 434,448

[22] Filed: Oct. 15, 1982

[51] Int. Cl.$^3$ .................. C07C 131/00; C07C 131/02; C07C 131/04; C07C 131/06; C07C 131/08; C07C 131/10

[52] U.S. Cl. .................. 560/21; 260/465 D; 560/22; 560/35; 562/434; 562/435; 562/437; 562/438; 562/440; 562/498; 562/499; 562/500; 562/501; 562/502; 562/503; 562/505; 562/506; 562/507; 562/560; 568/314; 568/346; 568/386; 568/391; 568/420; 568/433; 568/435; 568/465; 568/484

[58] Field of Search .............. 562/434, 435, 437, 438, 562/440, 560, 507, 498–503, 505, 506; 560/35, 22, 21; 260/465 D; 568/386; 564/256

[56] References Cited

U.S. PATENT DOCUMENTS

| | | | |
|---|---|---|---|
| 2,540,047 | 1/1951 | Hackmann | 564/266 |
| 4,306,900 | 12/1981 | Swithenbank et al. | 71/123 |
| 4,344,789 | 8/1982 | Krass | 562/435 |

FOREIGN PATENT DOCUMENTS

0052742  6/1982  European Pat. Off. ............ 564/256

OTHER PUBLICATIONS

*Journal of the American Chem. Society*, vol. 78, pp. 2469–2473, (1956), Newman et al., "A New Reagent for Resolution by Complex Formation".

*Primary Examiner*—Natalie Trousof
*Assistant Examiner*—Patricia M. Scott
*Attorney, Agent, or Firm*—Edward J. Whitfield

[57] ABSTRACT

Aldoxime or ketoxime-O-alkanoic acid is prepared by transoximation of an aldehyde or ketone, the reaction being conducted in a liquid phase at a pressure below one atmosphere. Conversion of the aldoxime or ketoxime-O-alkanoic acid to the ester or salt form is also described.

14 Claims, No Drawings

METHOD FOR PREPARING ALDOXIME OR KETOXIME-O-ALKANOIC ACID

FIELD OF THE INVENTION

This invention relates to a method for preparing aldoxime or ketoxime-O-alkanoic acid as well as esters and salts thereof.

SUMMARY OF THE INVENTION

In accordance with this invention, a desired aldoxime or ketoxime-O-alkanoic acid is prepared by reacting a ketone or aldehyde with a different aldoxime or ketoxime-O-alkanoic acid in an acidic liquid reaction medium at a pressure of less than one atmosphere and a temperature above the boiling point of the by-product aldehyde or ketone. The aldoxime or ketoxime-O-alkanoic acid product may, if desired, be converted to the ester or salt form.

DESCRIPTION OF THE INVENTION

The process of this invention may be schematically illustrated by the following reaction:

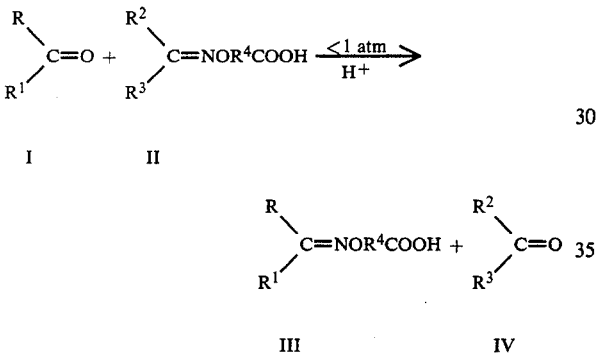

In the above-illustrated reaction, an aldehyde or ketone of the Formula I is reacted with an aldoxime or ketoxime-O-alkanoic acid of the Formula II, in an acidic liquid reaction medium to give the desired aldoxime or ketoxime-O-alkanoic acid of the Formula III and by-product ketone or aldehyde of the Formula IV. This reaction is commonly characterized as a transoximation reaction.

Since the boiling point of the by-product Formula IV compound is less than that of the desired product Formula III compound, it would be expected that straightforward fractional distillation would enable ready separation of these materials. However, it has been found that distillation at atmospheric pressure does not effectively remove the by-product Formula IV compound, which, in turn, leads to lower yields of product Formula III compound. It has been observed that the Formula IV compound can be most effectively removed by fractional distillation at less than atmospheric pressure, resulting in more rapid conversion of starting materials, with the extent of conversion in excess of 90 percent.

Consequently, in accordance with this invention, the reaction between the Formulae I and II compounds is conducted at less than atmospheric pressure and at a temperature above the boiling point of the Formula IV compound to enable removal of the Formula IV compound and a more rapid conversion to and a higher yield of desired Formula III compound.

The reaction between the Formula I and II compounds is conducted in a liquid reaction medium, preferably in an organic liquid reaction medium, that is capable of solubilizing the Formula I and II compounds. Suitable organic liquids include weak organic acids such as acetic acid or propionic acid; higher boiling alcohols such as propanol or butanol; polar aprotic solvents such as sulfolane, dimethylsulfoxide, or dimethylformamide. Acetic acid is preferred since it is readily available and relatively inexpensive. There is some reason to believe that the presence of a certain amount of water, e.g., up to about 10 weight percent, might be advantageous.

The liquid reaction medium also contains from about 5 percent to about 20 percent by weight, typically about 8 to 10 percent by weight, of a strong organic or mineral acid, e.g., p-toluene sulfonic acid, hydrochloric acid, sulfuric acid, or the like.

As beforesaid, the reaction temperature is maintained above the boiling point of the by-product aldehyde or ketone of the Formula IV. Typically the reaction temperature would be in the range of from about 50° C. to about 120° C. and preferably in the range of from about 70° C. to about 90° C. in the case where acetic acid or higher boiling solvents are used. For lower boiling solvents, the reaction temperature must, of course, be adjusted accordingly.

Although any subatmospheric pressure would enable removal of the Formula IV by-product aldehyde or ketone, the reaction is usually conducted at a pressure of from about 0.1 to about 0.6 atmosphere, preferably from about 0.2 to about 0.4 atmosphere.

Although any aldehyde or ketone of the Formula I may be used in the practice of this invention, i.e., R and $R^1$ may be the same or different and represent hydrogen or any organic radical, the invention is especially applicable to aldehydes and ketones wherein R represents hydrogen or $C_1$ to $C_4$ alkyl and $R^1$ represents radical of the Formula V:

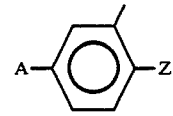

wherein Z is hydrogen, halogen (e.g., chlorine, bromine or fluorine), nitro or cyano; and A is nitro, halogen (e.g., chlorine, bromine or fluorine), or MO— wherein M is hydrogen, alkali metal (e.g., sodium or potassium) or the radical

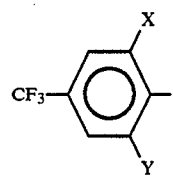

wherein X is hydrogen, halogen (e.g., chlorine, bromine or fluorine), trihalomethyl (e.g., trifluoromethyl), $C_1$ to $C_4$ alkyl or cyano; and Y is hydrogen or halogen (e.g., chlorine, bromine or fluorine).

Certain of the compounds represented by the Formula V are useful as herbicides or herbicide intermediates and are described in, for example, U.S. Pat. Nos.

4,306,900 and 4,344,789. Formula V compounds of particular interest are those wherein Z is nitro and A is

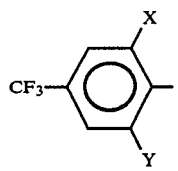

wherein X is halogen, preferably chlorine, and Y is hydrogen.

In like fashion, any aldoxime or ketoxime-O-alkanoic acid of the Formula II may be used providing, of course, that $R^2$ and $R^3$ are not respectively identical to R and $R^1$ of the Formula I aldehyde or ketone. With this proviso in mind, $R^2$ and $R^3$ can be the same or different and represent hydrogen or any organic radical; however, $R^2$ and $R^3$ preferably are the same or different $C_1$ to $C_4$ alkylene, preferably methylene.

The Formula II compound may be prepared in known fashion by reacting an aldoxime or ketoxime of the formula $R^2R^3CNOH$ with a suitable haloalkanoic acid of the formula Hal—$R^4$—COOH wherein Hal is halogen, preferably bromine or chlorine and $R^4$ is a linear or branched $C_1$ to $C_3$ alkylene radical. Exemplary aldoximes and ketoximes are disclosed, for example, in U.S. Pat. No. 2,540,047; whereas haloacetic acid, halopropionic acid, halobutyric acid and the like are exemplary of suitable haloalkanoic acids.

This invention also contemplates preparation of esters and salts of the Formula III compounds. Esters of the Formula III compounds are prepared is known fashion by, for example, reacting the Formula III compound with an aliphatic alcohol of the formula $R^5$—OH, wherein $R^5$ is linear or branched $C_1$ to $C_{10}$ alkyl. The esterification reaction is typically conducted at up to reflux temperature in the presence of a strong organic or mineral acid, such as, for example, p-toluene sulfonic acid, hydrochloric acid, or sulfuric acid, for a time sufficient to effect the required degree of esterification.

Salts of the Formula III compounds are readily prepared, in known fashion, by reaction with an inorganic or organic base. Exemplary inorganic bases include alkali or alkaline earth metal hydroxides or carbonates such as sodium, potassium, lithium, or calcium hydroxides or carbonates. Ammonia, ammonium hydroxide, trimethylamine, or ethanolamine are exemplary of suitable organic bases.

It is additionally within the province of this invention to prepare esters and salts of the Formula III compounds by first esterifying or converting to the salt form the Formula II compound and then reacting the same with the Formula I compound under the process conditions described hereinabove.

Alternatively, the Formula II compound, per se, or in its ester or salt form, may be first subjected to acid hydrolysis to liberate the aldehyde or ketone with the resulting aminooxyalkanoic acid (or ester or salt thereof) being reacted with the Formula I compound in the abovedescribed fashion.

A preferred embodiment of the process of this invention is illustrated by the following Examples, which are intended to illustrate, but not to limit the scope thereof.

EXAMPLE I

The reactor used in this experiment was a one-liter capacity, 4-necked flask provided with a condenser and vacuum take-off, a thermo-watch, a vacuum relief valve, and a magnetic stirring bar. A manometer was installed between the vacuum take-off line and the residue trap. One of the necks of the flask was filled with a removable stopper to facilitate charging and sampling. 120 Grams (0.33 mole) of 5-(2-chloro-4-trifluoromethylphenoxy)-2-nitroacetophenone was dissolved in 250 milliliters of acetic acid by heating at 55° C. to 60° C., and this warm solution was charged to the reactor. 48.0 Grams (0.36 mole) of isopropylidine aminooxyacetic acid and 12.5 grams (0.066 mole) of p-toluene sulfonic acid were then washed into the reactor with 50 milliliters of acetic acid. 15 Milliliters of water were then added. The system was placed under a vacuum of 225 to 230 millimeters of mercury (about 0.3 atmosphere), the thermowatch was set to control at 85° C., and the reaction mixture was stirred overnight under these conditions.

After 18 hours, HPLC analysis indicated conversion of starting materials to be 84.7 percent complete. An additional 5 milliliters of water and an additional 6.2 grams of p-toluene sulfonic acid were added and stirring was continued under vacuum at 85° C. After 21 hours, HPLC analysis of a sample of the reaction mixture indicated conversion of 93 percent. Stirring was continued under the same conditions of temperature and pressure. After 24 hours, HPLC analysis indicated conversion of 96.5 percent. Heating and vacuum were discontinued, and the reaction mixture was then stripped of acetic acid solvent, yielding 182 grams of an oily residue which was dissolved in 200 milliliters of methylene chloride. This solution was seeded with a small quantity of p-toluene sulfonic acid and was permitted to stand overnight at ambient temperature. The solid precipitate which formed on standing was filtered off, washed with methylene chloride and air dried, affording 5.7 grams of a white solid, which was discarded. The filtrate was then washed with water and saturated aqueous sodium chloride solution and dried over anhydrous magnesium sulfate. Subsequent filtration and evaporation of solvent afforded 156.1 grams of a dark viscous oil identified as the desired product, 5-(2-chloro-4-trifluoromethylphenoxy)-2-nitroacetophenone oxime-O-acetic acid.

EXAMPLE II

To a flask provided with a reflux condenser and drying tube was charged all of the 5-(2-chloro-4-trifluoromethylphenoxy)-2-nitroacetophenone oxime-O-acetic acid (prepared as described in Example I) dissolved in one liter of methanol. 2.0 Grams of p-toluene sulfonic acid were added and the reaction mixture was heated and maintained at reflux for 3 hours, at which time HPLC analysis indicated only about one percent unesterified acid. Heating was discontinued and the reaction mixture was stripped of solvent to a total volume of about 600 milliliters. After standing overnight in a stoppered flask, the reaction mixture was cooled in an ice bath for about 2 hours and the solid precipitate was filtered off and washed with cold methanol. After air drying for about 2 hours, 126.1 grams of solid was obtained, corresponding to an 83 percent yield of 97.2 percent assay, 5-(2-chloro-4-trifluoromethylphenoxy)-

2-nitroacetophenone oxime-O-(acetic acid, methyl ester).

EXAMPLE III (COMPARISON)

The reactor used in this experiment was a three-liter capacity flask provided with a mechanical stirring assembly, a fritted glass tube positioned to bubble nitrogen gas below the surface of the reaction mixture, and a Claisen Head with a thermowatch and a continuous distillation head attached. The flask was charged with 359 grams (1.0 mole) of 5-(2-chloro-4-trifluoromethylpheonxy)-2-nitroacetophenone and 1500 milliliters of acetic acid. To this stirred solution was added 65.5 grams (0.5 mole) of isopropylidene aminooxyacetic acid and 4.75 grams (0.025 mole) of p-toluene sulfonic acid. Nitrogen was bubbled into the reaction mixture at a moderate rate and heating was started. After 20 minutes' heating, the pot temperature was 47° C., and all of the reactant had gone into solution. After 1 hour and 17 minutes, the pot temperature was 112° C. and a sample was submitted for HPLC analysis, which indicated a conversion of about 2 percent. After 1 hour and 23 minutes, the first drops of distillate were collected at a head temperature of 97° C. and a pot temperature of 115° C. The thermowatch was then set on the head thermometer to control at 100° C. HPLC analysis of a sample taken 4 hours and 16 minutes after initiation of the reaction indicated conversion of 5.2 percent.

After about 24 hours of reaction under the aforesaid conditions, HPLC analysis indicated a conversion of 8.3 percent. An additional 32.75 grams (0.25 mole) of isopropylidene aminooxyacetic acid and 4.75 grams (0.025 mole) of p-toluene sulfonic acid were added and the nitrogen purge was discontinued since it did not appear to have any positive effect on the reaction.

After about 26 additional hours (total reaction time of about 50 hours) of stirring at reflux, HPLC analysis indicated a conversion of 21.3 percent. 32.75 Grams (0.25 mole of isopropylidene aminooxyacetic acid and 4.75 grams (0.025 mole) of p-toluene sulfonic acid were then added. After about an additional 23 hours reaction (total reaction time of about 73 hours), HPLC analysis indicated conversion of 29.7 percent. 4.75 Grams (0.025 mole) of p-toluene sulfonic acid was added and reflux was continued for about an additional 22 hours (total reaction time about 95 hours), at which time HPLC analysis indicated a conversion of 38 percent. After stirring at reflux for about an additional 24 hours (total reaction time about 119 hours), during which time 9.5 grams of p-toluene sulfonic acid was added in two equal portions some hours apart, conversion had risen to 50.9 percent as indicated by HPLC analysis. Stirring at reflux was continued for about another 24 hours (total reaction time of about 143 hours) during which time 9.5 grams of p-toluene sulfonic acid were again added in two equal portions. HPLC analysis at this point indicated conversion at 59.1 percent. Addition of 4.75 grams of p-toluene sulfonic acid and continued stirring at reflux for about an additional 31 hours (total reaction time of about 174 hours) showed an increase in conversion to 63 percent.

At this point 13.1 grams of isopropylidene aminooxyacetic acid and 1.23 grams of concentrated sulfuric acid were added and stirring at reflux was continued an additional three days (total reaction time of about 246 hours). The reaction was then discontinued since HPLC analysis indicated an increase in conversion of only 4 percent to 67 percent.

EXAMPLE IV

The reactor used in this experiment was a 500 milliliter capacity, 5-necked flask equipped as described in Example I. The reactor was charged with 24.17 grams of 3-fluoroacetophenone, 150 milliliters of acetic acid and 24.89 grams of isopropylidene aminooxyacetic acid. 6.65 Grams of p-toluene sulfonic acid was rinsed into this stirred solution with 50 milliliters of acetic acid and 10 milliliters of water. After about 2 hours reaction at 17° to 22° C. and a pressure of about 0.36 atmosphere, HPLC analysis indicated conversion of about 16 percent.

The reaction mixture was heated to 45° to 50° C. under a slight vacuum; and after 6 hours heating at 45° to 50° C. HPLC analysis indicated 53.3 percent conversion. After stirring overnight at 45° to 50° C., the temperature was raised to 60° C. After 3½ hours at 60° C. and a pressure of about 0.31 atmosphere, conversion had reached about 70 percent.

One gram of p-toluene sulfonic acid and 5 milliliters of water were added and the temperature was increased to 60° to 65° C. After 1.25 hours at this temperature conversion had reached about 77 percent as indicated by HPLC analysis. Following the addition of one gram p-toluene sulfonic acid, 10 milliliters of water, and 25 milliliters of acetic acid, a total of 4 hours heating at 60° to 65° C. at a pressure of about 0.35 atmosphere, conversion had reached 78.8 percent.

10 milliliters of water were added and the temperature was adjusted to 80° to 85° C. After 2 hours reaction at this temperature and a pressure of about 0.38 atmosphere, conversion had risen to 82.8 percent. After addition of 10 milliliters of water and 25 milliliters of acetic acid, the reaction mixture was stirred overnight at 80° to 85° C. and about 0.38 atmosphere. HPLC analysis after 13 hours reaction, under these conditions, indicated conversion of 89.9 percent.

After the addition of milliliters of water and 25 milliliters of acetic acid and 25 hours reaction at 80° to 85° C. and about 0.38 atmosphere conversion had reached 91.7 percent. Following the addition of 10 milliliters of water and 10 milliliters of acetic acid and 39.25 hours reaction at 80° to 85° C. and 0.38 atmosphere, 92.9 conversion was indicated by HPLC analysis. After the addition of 10 milliliters of water and 15 milliliters of acetic acid and a total of 60.25 hours reaction at 80° to 85° C. and 0.38 atmosphere, conversion had reached 94.4 percent, at which point, the reaction was terminated.

A comparison of the experimental results described in Examples I and III dramatically shows the improvement obtained by conducting the transoximation reaction at less than atmospheric pressure in accordance with this invention. When the reaction of Example I was terminated about 24 hours after it was initiated, conversion of starting materials was 96.5 percent complete. In contrast, in the reaction of Example III, conversion after 24 hours was only 8.3 percent and when the reaction was terminated some 10 days after it was initiated, conversion has reached only 67 percent.

Although the process of this invention has been illustrated in some detail by the foregoing Examples, it is to be understood that many variations may be made therein simply by varying the choice of starting materials. It must be emphasized that the crux of this invention resides in removing by-product aldehyde or ketone from the reaction mixture at less than atmospheric pressure to enhance conversion to and yield of desired aldoxime or ketoxime-O-alkanoic acid product.

We claim:

1. A process for preparing aldoxime or ketoxime-O-alkanoic acid of the formula:

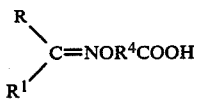

wherein R and $R^1$ are the same or different and represent hydrogen or an organic radical and $R^4$ is linear or branched $C_1$ to $C_4$ alkylene, by reacting an aldehyde or ketone of the formula:

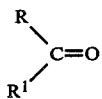

with an aldoxime or ketoxime-O-alkanoic acid of the formula:

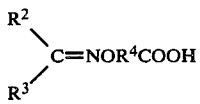

wherein R, $R^1$ and $R^4$ are as previously defined and $R^2$ and $R^3$ are the same or different and represent hydrogen or an organic radical, with the proviso that $R^2$ and $R^3$ are not respectively identical with R and $R^1$, in a liquid organic reaction medium containing a strong organic or mineral acid at a temperature above the boiling point of the by-product aldehyde or ketone of the formula:

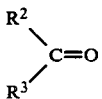

wherein $R^2$ and $R^3$ are as previously defined and at a pressure of from about 0.1 to about 0.6 atmosphere.

2. The process of claim 1 werein the reaction is conducted at temperature of from about 50° C. to about 120° C.

3. The process of claim 2 wherein the reaction temperature is from about 80° C. to about 90° C.

4. The process of claim 1 wherein the pressure is from about 0.2 to about 0.4 atmosphere.

5. The process of claim 1 wherein R is hydrogen or $C_1$ to $C_4$ alkyl and $R^1$ is the radical

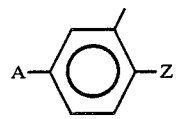

wherein Z is hydrogen, halogen, nitro or cyano; and A is nitro, halogen or M— wherein M is hydrogen, alkali metal or the radical,

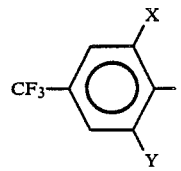

wherein X is hydrogen, halogen, trihalomethyl, $C_1$ to $C_4$ alkyl or cyano; and Y is hydrogen or halogen.

6. The process of claim 5 wherein $R^1$ is the radical

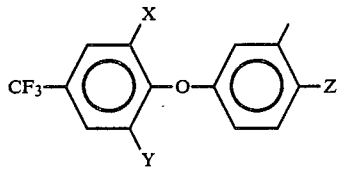

wherein:
X is hydrogen, halogen, trihalomethyl, $C_1$ to $C_4$ alkyl or cyano;
Y is hydrogen or halogen; and
Z is hydrogen, halogen, cyano, or nitro.

7. The process of claim 6 wherein R is methyl, X is chlorine, Y is hydrogen, and Z is nitro.

8. A process for preparing 5-(2-chloro-4-trifluoromethylphenoxy)-2-nitroacetophenoneoxime-O-(acetic acid, methyl ester) by reacting, in an organic liquid medium and in the presence of a strong inorganic or organic acid, 5-(2-chloro-4-trifluoromethylphenoxy)-2-nitroacetophenone with isopropylidene aminooxyacetic acid, at a temperature of from about 50° C. to about 120° C. and a pressure of from about 0.1 to about 0.6 atmosphere and esterifying the reaction product with methyl alcohol in the presence of a strong inorganic or organic acid.

9. The process of claim 8 wherein the temperature is from about 80° C. to about 90° C.

10. The process of claim 8 wherein the pressure is from about 0.2 to about 0.4 atmosphere.

11. The process of claim 8 wherein the organic liquid is acetic acid.

12. The process of claim 8 wherein the liquid reaction medium contains up to about 10 weight percent of water.

13. The process of claim 8 wherein the strong acid is selected from p-toluene sulfonic acid, hydrochloric acid, or sulfuric acid.

14. The process of claim 13 wherein the acid is p-toluene sulfonic acid.

* * * * *

UNITED STATES PATENT AND TRADEMARK OFFICE
CERTIFICATE OF CORRECTION

PATENT NO. : 4,504,671

DATED : March 12, 1985

INVENTOR(S) : Dennis K. Krass, John C. Crano & Melvin S. Newman

It is certified that error appears in the above-identified patent and that said Letters Patent is hereby corrected as shown below:

Column 8, line 9, "M—" should be --MO---.

Signed and Sealed this

Ninth Day of July 1985

[SEAL]

Attest:

DONALD J. QUIGG

Attesting Officer     Acting Commissioner of Patents and Trademarks